(12) United States Patent
Holmstrom et al.

(10) Patent No.: US 9,138,583 B2
(45) Date of Patent: Sep. 22, 2015

(54) METHOD AND SYSTEM FOR DETERMINING PACING SETTINGS

(75) Inventors: Nils Holmstrom, Jarfalla (SE); Andreas Karlsson, Solna (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 162 days.

(21) Appl. No.: 13/596,585

(22) Filed: Aug. 28, 2012

(65) Prior Publication Data

US 2013/0053915 A1 Feb. 28, 2013

Related U.S. Application Data

(60) Provisional application No. 61/539,041, filed on Sep. 26, 2011.

(30) Foreign Application Priority Data

Aug. 31, 2011 (EP) .................................... 11179568

(51) Int. Cl.
*A61N 1/362* (2006.01)
*A61N 1/365* (2006.01)
*A61N 1/37* (2006.01)
*A61N 1/368* (2006.01)

(52) U.S. Cl.
CPC .......... *A61N 1/36514* (2013.01); *A61N 1/3682* (2013.01); *A61N 1/3704* (2013.01); *A61N 1/365* (2013.01)

(58) Field of Classification Search
CPC ............. A61N 1/00; A61N 1/02; A61N 1/04; A61N 1/05; A61N 1/08; A61N 1/025; A61N 1/362; A61N 1/372
See application file for complete search history.

(56) References Cited

U.S. PATENT DOCUMENTS

| | | | |
|---|---|---|---|
| 5,836,987 A | 11/1998 | Baumann et al. | |
| 6,044,298 A | 3/2000 | Salo et al. | |
| 6,129,744 A | 10/2000 | Boute | |
| 6,253,106 B1 | 6/2001 | Legay et al. | |
| 7,313,439 B2 | 12/2007 | Jackson et al. | |
| 2006/0161209 A1 | 7/2006 | Pastore et al. | |
| 2008/0058874 A1 | 3/2008 | Westlund et al. | |
| 2010/0030295 A1 | 2/2010 | Whinnett et al. | |
| 2011/0015704 A1 | 1/2011 | Ternes et al. | |

OTHER PUBLICATIONS

Ext. European Search Report, dated Nov. 11, 2011—EP App. No. 11179568.8.

*Primary Examiner* — Christopher D Koharski
*Assistant Examiner* — Elizabeth K So

(57) ABSTRACT

Systems and methods for optimizing the stimulation of a heart of a patient are disclosed herein. The method comprises delivering pacing therapy to the patient according to a pacing therapy setting schedule, using specific pacing intervals via specific electrode configurations. Further, sinus rate values are recorded over at least one cardiac cycle at each pacing therapy setting and it is determined whether a sinus rate value satisfies predetermined measurement conditions, wherein sinus rate values are used for trending the sinus rate over time if the measurement conditions are satisfied. The accepted sinus rate values, i.e. values that satisfy the measurement conditions, are trended over time, wherein each trended sinus rate value is created based on recordings from at least one cardiac cycle. A preferred pacing therapy setting is determined to be the pacing therapy setting that provides a lowest sinus rate.

9 Claims, 6 Drawing Sheets

METHOD AND SYSTEM FOR DETERMINING PACING SETTINGS

CROSS REFERENCE TO RELATED APPLICATIONS

This application claims priority from European Patent Application No. 11179568.8, filed Aug. 31, 2011, and U.S. Provisional Patent Application Ser. No. 61/539,041, filed Sep. 26, 2011.

FIELD OF THE INVENTION

The present invention relates generally to implantable medical devices and more particularly to systems and methods for optimizing the stimulation of a heart of a patient.

BACKGROUND OF THE INVENTION

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as the subcutaneous pocket. The implantable devices generally function in association with one or more electrodes carrying leads which are implanted within the heart. The electrodes are positioned within the heart for making electrical contact with the muscle tissue of their respective heart chamber. Conductors within the leads connect the electrodes to the device to enable the device to deliver the desired electrical therapy.

Monitoring heart rate at a defined degree of workload is a good parameter to use when monitoring the status of a patient's cardiovascular function and oxygen uptake as well as pacing therapy settings including pacing intervals and pacing sites. Rest rate is often associated with a patient's exercise capacity and health. During hard training the rest rate will decrease as the heart becomes stronger and oxygen uptake and metabolism are improved. The change in rest rate is normally slow and sudden changes depend most often on factors like fever, body posture changes or changes in atmospheric pressure. Cardiac output (CO) is the heart rate (HR) multiplied with the stroke volume (SV).

Regulation of blood flow in the various organs is mainly achieved by narrowing the blood vessels, vasoconstriction, and widening of blood vessels, vasodilation. This tonus of the vascular musculature is influenced by local effects, neural activity and hormonal signals. At rest, most blood vessels are in an intermediate state of tension and relatively constant.

Adaptation of SV to changes in filling and aortic pressure takes place autonomously, by alterations of the end-diastolic resting tension, i.e. the Frank-Starling mechanism. If this regulation is impaired or fails due to suboptimal pacemaker settings, the heart tries to compensate for this by an increased sinus rhythm to maintain the cardiac output. Thus, reduced SV can be associated with suboptimal settings of pacing intervals such as AV delay and VV delay and/or pacing sites. In short term, this will be compensated by an increased heart rate to maintain a sufficient cardiac output. In the long term, the stroke volume may increase towards the initial value due to hypertrophy and heart dilatation and thus the heart rate will decrease again.

The heart rate depends of several factors like activity level, body temperature, atmospheric pressure, stress, vascular resistance and body posture. To monitor changes of the heart rate due to variations of the pacing therapy settings, it is important to have knowledge of these parameters so that the heart rate can be compared at similar or same conditions.

In the art, there have been made significant efforts to develop methods and devices for optimizing pacing therapy settings and/or monitoring diseases based on heart rate.

For example, in US patent application No. 2010/0030295 to Whinnett et al, a method for determining optimal AV delay while pacing at rest heart rate is disclosed. Optimal AV delay is considered to have been found when the highest blood pressure is achieved.

In the international patent application No. WO 2011/008749 to Ternes et al., an implanted device that trends heart rate, both during and without stimulation, and the stimulation changes when average rest heart rate is changed is disclosed.

In U.S. Pat. No. 6,129,744 to Boute, a method for determining heart failure conditions by studying and trending changes in rest rates is disclosed. The result is indicative of the onset of LVD ("Left Ventricular Dysfunction") and corresponding ejection fraction.

In U.S. Pat. No. 7,3131,439 to Jackson et al., a method for predicting arrhythmias based on trending heart rates is disclosed.

However, there is still a need within the art for improved methods, devices and systems for optimizing cardiac pacemakers.

SUMMARY OF THE INVENTION

The present invention provides systems and methods for improvements in the optimization of pacing therapy settings such as AV and/or VV delays or electrode configurations. More specifically, at least some aspects of the present invention provides improved systems and methods for utilizing the sinus rhythm as guidance when optimizing pacing therapy settings such as AV and/or VV delays or electrode configurations.

For example, according to an aspect of the present invention, there is provided a method for pacing therapy optimization of a cardiac stimulator implanted in a patient. The method comprises delivering pacing therapy to the patient according to a pacing therapy setting schedule, wherein a pacing therapy setting according to the pacing therapy setting schedule comprises delivery of pacing stimulation using specific pacing intervals via specific electrode configurations, over a range of pacing therapy settings. Further, sinus rate values are recorded over at least one cardiac cycle at each pacing therapy setting and it is determining whether a sinus rate value satisfies predetermined measurement conditions, wherein sinus rate values are used for trending the sinus rate over time if the measurement conditions are satisfied. The accepted sinus rate values, i.e. values that satisfy the measurement conditions, are trended over time, wherein each trended sinus rate value is created based on recordings from at least one cardiac cycle. A preferred pacing therapy setting is determined to be the pacing therapy setting that provides a lowest sinus rate.

According to another aspect of the present invention, there is provided a system for pacing therapy optimization of a cardiac stimulator implanted in a patient. The system comprises a pacing delivery module configured to deliver pacing therapy to the patient according to a pacing therapy setting schedule, wherein a pacing therapy setting according to the pacing therapy setting schedule comprises delivery of pacing stimulation using specific pacing intervals via a specific electrode configuration, over a range of pacing therapy settings. A cardiac data recording module is configured to record sinus rate values over at least one cardiac cycle for different pacing therapy settings. An analyzing module is configured to determine whether a sinus rate value satisfies predetermined measurement conditions, wherein the sinus rate value is used for trending the sinus rate if the measurement conditions are satisfied. Further, the analyzing module is configured to trend the sinus rate over time, wherein each trended sinus rate value is created based on recordings from at least one cardiac cycle and determine a preferred pacing therapy providing a lowest sinus rate based on a trend analysis of the sinus rate.

Thus, the present invention is based on the idea of trending sinus rate values during defined measurement conditions to detect changes of optimal pacing therapy settings, such as AV and VV delays or pacing sites, of an implanted device. An automatic and iterative re-programming of the pacing therapy settings are used to continuously optimize the device with guidance of the sinus rate response. An increase of the sinus rate (i.e. higher sinus rate values) during the defined measurement conditions, preferably during rest, and optionally at defined atmospheric pressure, body temperature and body posture, after re-programming is an indication of an impaired contractile function with a reduced stroke volume. A decreased sinus rate (i.e. lower sinus rate values) is on the other hand an indication of a more optimal pacing therapy setting. Because the algorithm continuously optimizes the pacing therapy settings, it can be ensured that an optimal pacing therapy is achieved also when reverse remodelling changes the optimal pacing therapy settings. Hence, the sinus rhythm is used as a sensor for pacemaker setting optimization. During this optimization, the atrioventricular (AV) delays and interventricular (W) delays are continuously changed in small increments within certain boundaries until the lowest sinus rate has been found, and thus until the cardiac work is as its lowest. Further, different pacing sites can be tested to find the most optimal electrode configuration based on the sinus rate response. The pacing site and/or pacing intervals (e.g. AV and VV delays) are adjusted according to a pacing therapy setting schedule, which may be pre-programmed or predetermined. For example, different pacing sites may be RV (right ventricle), LV (left ventricle), RA (right atrium), LA (left atrium), endocardial, sub-endocardial, epicardial or intramural. Furthermore, pacing modalities can be optimized. For example, the heart can be stimulated at several locations simultaneously or with a time delay in order to improve the contraction and hemodynamics. The optimal multisite combination can be determined using the present invention. Moreover, a location of a leadless pacemaker can also be determined during the implantation procedure.

In at least one embodiment the reprogramming of the device is based on representative data since, as mentioned above, a reduced stroke volume associated with suboptimal pacing therapy settings, e.g. suboptimal programming of AV-, VV, intra-ventricular delays in dual chamber and CRT devices and/or suboptimal pacing sites, will in the short term be compensated for by an increased heart rate to maintain sufficient cardiac output to meet the metabolic demands. However, in order to serve as an indirect sensor of the response in stroke volume changes, the sinus rate must be measured under defined measurement conditions. Because the autonomic heart rate regulation depends on several parameters, changes of the heart rate have to be evaluated to identify alternative causes of an observed rate change. Therefore, according to embodiments of the present invention, different sensors are used to monitor different internal (intra corporeal) and/or external (extracorporeal) heart rate influencing factors. For example, an accelerometer can be used to monitor an activity level of the patient, a thermometer can be used to measure the central body temperature, a pressure sensor can be used to measure an atmospheric pressure, and an accelerometer can be used to determine a body posture, e.g. whether the patient is supine or upright. Circadian variations can be avoided by measuring the sinus rate values during the same time of the day, for example when the patient is at rest during night-time, which can be determined by time, i.e. by an internal clock, and the activity sensor (e.g. an accelerometer).

According to an embodiment of the present invention, pacing therapy is delivered to the patient according to a pacing therapy setting schedule, including delivering pacing therapy via at least two different electrode configurations and a number of heart cycles for each electrode configuration. Each sinus rate value is recorded over at least one cardiac cycle for each pacing interval for each electrode configuration. Further, it is determined whether a sinus rate value satisfies predetermined measurement conditions, wherein sinus rate values are used for trending the sinus rate over time if the measurement conditions are satisfied. A preferred pacing therapy setting including a preferred electrode configuration and a preferred pacing interval is determined to be the pacing therapy setting that provides the lowest sinus rate based on a trend analysis of the sinus rate values. Hence, the optimization is performed on two levels. The electrode configuration or pacing site selection is evaluated in that a set of timing intervals, e.g. VV intervals, are tested to find the optimal timing interval for the selected electrode configuration or pacing site, i.e. the timing interval providing the lowest sinus rate for the selected electrode configuration or pacing site. Thereafter, the same procedure is repeated for a next electrode configuration or pacing site to find the optimal timing interval for that electrode configuration or pacing site, i.e. the timing interval providing the lowest sinus rate for that selected electrode configuration or pacing site. Finally, the optimal combinations for each configuration are compared to find the final or overall optimal combination of electrode configuration and timing interval.

In one embodiment of the present invention, the recording of the sinus rate values for one pacing therapy setting is performed during a period of 24 hours or more, a floating average of the sinus rate over a period equal to a fraction of the recording period (i.e. 24 hours or more) is used as sinus rate values in the optimization process. The fraction may be, for example, 1-60 minutes.

According to embodiments of the present invention, the median or average values of the sinus rate and sensor signals providing information of different measurement condition parameters are calculated over relatively long periods of time, e.g. 5-120 min, and are stored in a memory of the implanted device. Depending on the input from the sensors, the sinus rate values are included in a trend analysis or are discarded. For example, sinus rate values obtained at increased workload, fever, changed altitude, or at an upright position are discarded.

According to embodiments of the present invention, a duration of a sinus rate increase or decrease must persist for a predetermined relatively long period of time, e.g. 2 hours, 12 hours, 24 hours, 36 hours, or 48 hours, before the increase or decrease is approved as a valid rate change. Similarly, the magnitude of the sinus rate increase must also be higher than a predetermined value, e.g. an increase or decrease of 40 ms, 50 ms, or 60 ms, in order to be qualified as a valid sinus rate change.

According to embodiments of the present invention, a value of the sinus rate determined over a predetermined period of time, e.g. an average sinus rate or median sinus rate determined based on sinus rate values obtained during the period of time, recorded at a previous pacing therapy setting is compared with a value of the sinus rate determined over a predetermined period of time recorded at a present pacing therapy setting and the pacing therapy setting providing the lowest value of the sinus rate is selected as the preferred pacing therapy setting.

According to an embodiment of the present invention, a pacing therapy setting may be determined to be a baseline setting. If a new pacing therapy setting is found that provide a lower sinus rate, e.g. an average sinus rate or median sinus rate determined based on sinus rate values obtained during a predetermined period of time, the new pacing therapy setting replace the previous pacing therapy setting as baseline setting. Preferably, the base setting is determined based on sinus rate values recorded during rest.

These and other features, aspects and advantages of the invention will be more fully understood when considered with respect to the following detailed description, appended claims and accompanying drawings.

BRIEF DESCRIPTION OF THE DRAWINGS

The drawings are not necessarily drawn to scale and illustrate generally, by way of example, but no way of limitation, various embodiments of the present invention. Thus, exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. For example, embodiments may be used with a pacemaker, a cardioverter, a defibrillator, and the like.

As used herein, the term "module" refers to an application specific integrated circuit (ASIC), an electronic circuit, a processor (shared, dedicated, or group) and memory that execute one or more software programs, a combinational logic circuit, or other suitable components that provide the described functionality.

Figure 1:
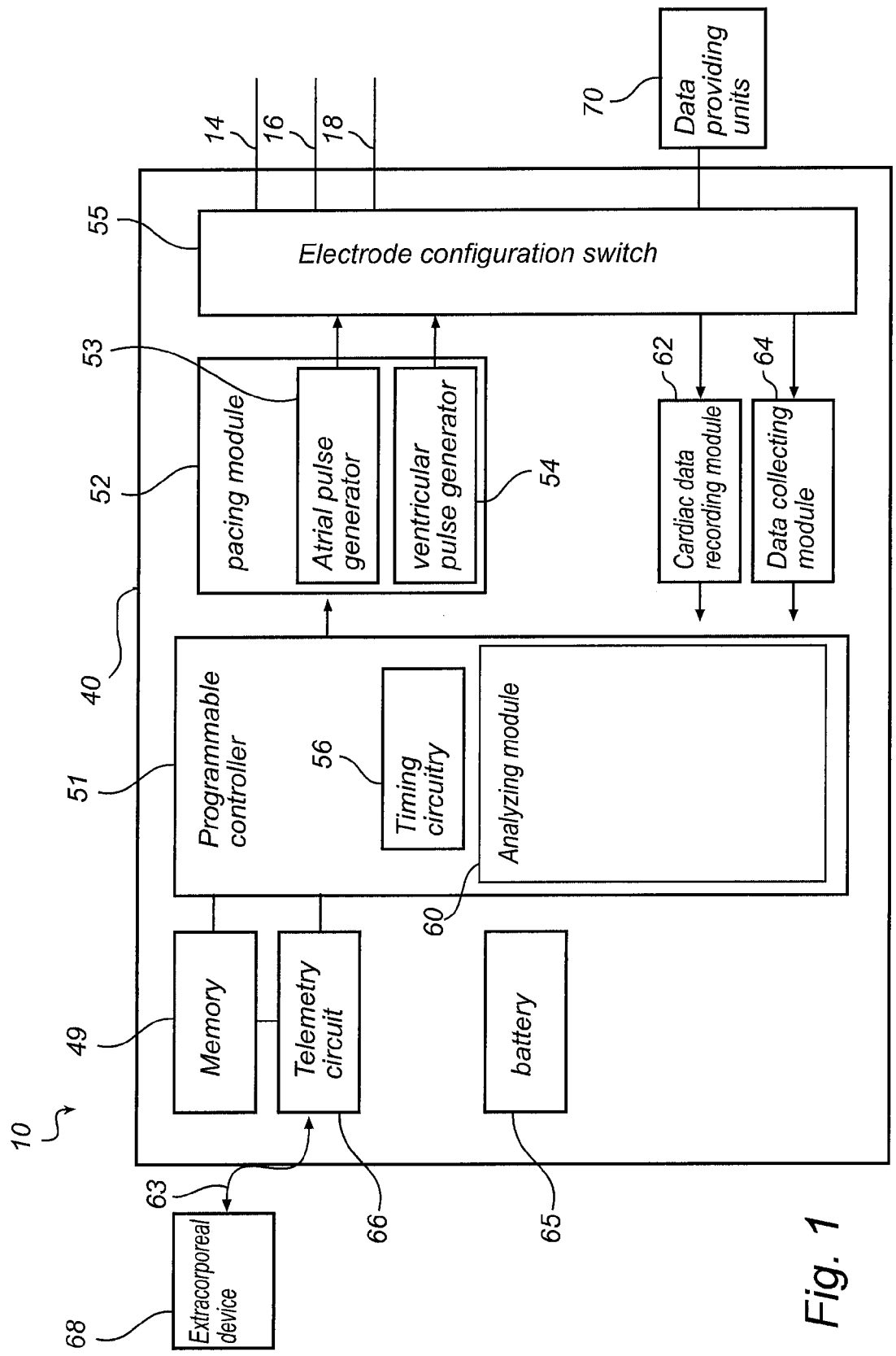
FIG. 1 is a simplified functional block diagram of one embodiment of a system in accordance with the present invention, illustrating basic elements of the system.

In FIG. 1, an exemplary, simplified block diagram depicting various components of the cardiac stimulator according to embodiments of the present invention is shown. The cardiac stimulator 10 is capable of delivering cardiac therapy via different electrode pairs and is configured to integrate both monitoring and therapy features, as will be described below. Further, the cardiac stimulator 10 is capable of collecting and processing data about the heart 12 (see FIG. 2) from electrode pairs for sensing cardiac electrogram (EGM) signals. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation.

The cardiac stimulator 10 has a housing 40, often referred to as the "can" or "case electrode". The housing 40 may function as a return electrode in "unipolar" modes. Further, the housing 40 includes connector (not shown) having a plurality of terminals (not shown) for connection with electrodes and/or sensors.

The cardiac stimulator 10 includes a programmable microcontroller or control module 51 that inter alia controls the various modes of stimulation therapy. As is well known within the art, the microcontroller 51 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 51 includes the ability to process or monitor input signals (data or information) as controlled by a program stored in a designated block of memory. The type of microcontroller is not critical to the described implementations. Rather, any suitable microcontroller 51 may be used that carries out the functions described herein. The use of micro-processor based control circuits for performing timing and data analysis are well known in the art.

Figure 2:
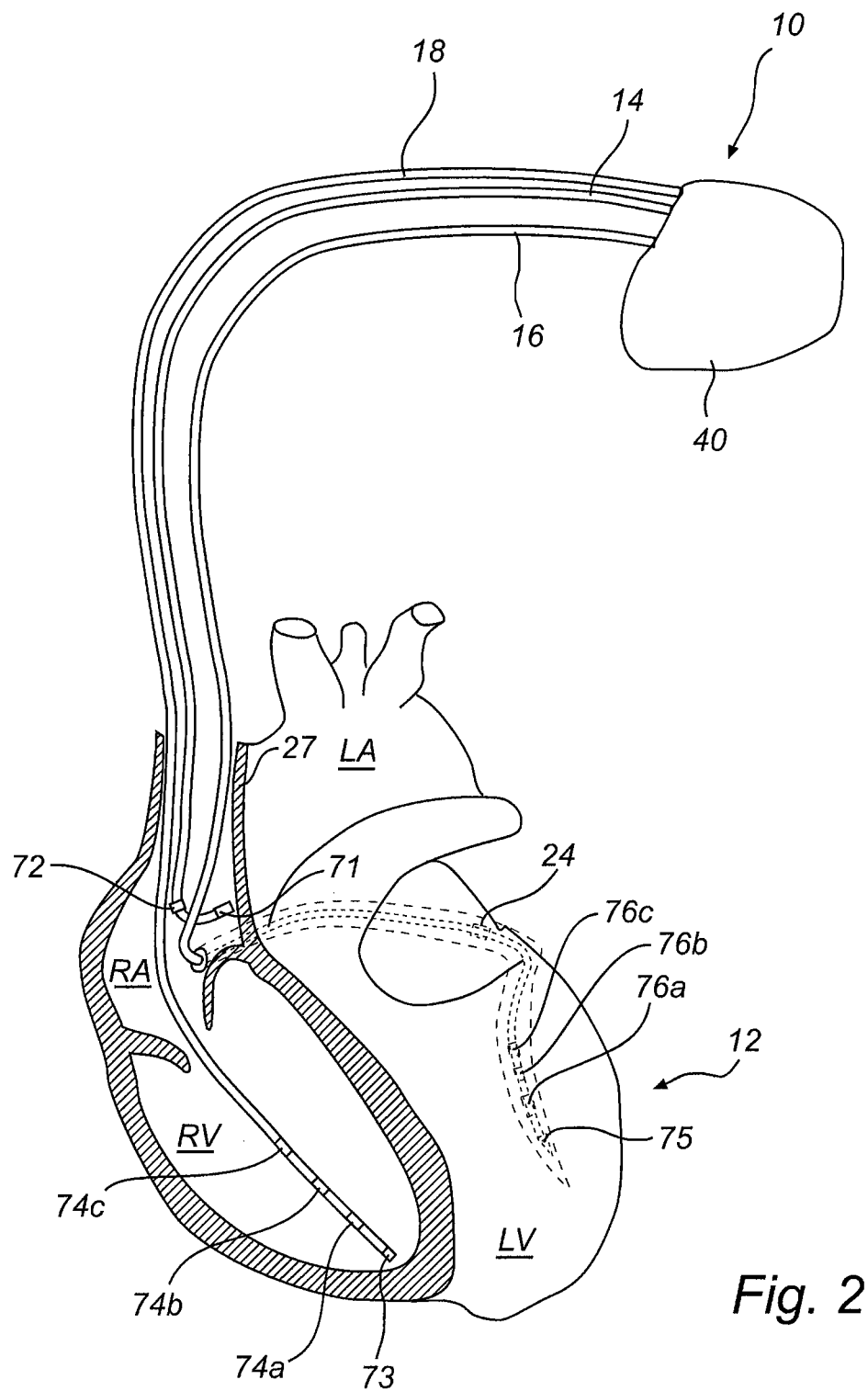
FIG. 2 is a simplified and schematic diagram of one embodiment of a system configuration according to the present invention including an implantable stimulation device in electrical communication with several leads implanted in a patient's heart for detecting cardiac activity and for delivering multi-chamber stimulation.

Furthermore, the cardiac stimulator 10 includes pacing module 52 adapted to provide pacing signals for delivery to the patient. The pacing module 52 comprises an atrial pulse generator 53 and a ventricular pulse generator 54 that generate pacing stimulation pulses for delivery by leads 14, 16, and 18 via an electrode configuration switch 55. In FIG. 2, an embodiment including a right atrial lead 14, a coronary sinus lead 16, and a right ventricular lead 18 is shown.

It is understood that in order to provide stimulation therapy in each of the four chambers, the atrial and ventricular pulse generators 53 and 54, may include dedicated, independent pulse generators, multiplexed pulse generators, or shared pulse generators. The pulse generators 53 and 54 are controlled by the microcontroller 51 via appropriate control signals to trigger or inhibit stimulation pulses.

A cardiac data recording module 62 is adapted to collect, for example, cardiac signals such as IEGM signals and record the cardiac signals. More specifically, the cardiac data recording module 62 is configured to collect and record IEGM signals, convert raw analog data into digital IEGM signals and determine sinus rate values from the IEGM signals. The sinus rate values can be stored in a memory for later processing or provided to an analyzing module 60 for further processing. The cardiac data recording module 62 may for this purpose interact with an ECG unit (not shown) that provides electrical impulses or other observed signals that can be used to model the patient's ECG waveform.

A data collecting module 64 is configured to collect measurement condition information corresponding to measurement condition parameters, which parameters include, for example, activity level information of the patient; and/or central body temperature of the patient; and/or atmospheric pressure; and/or a body posture of the patient, and/or time point of the day when the measurements are made.

The data collecting module 64 suitably interacts with one or more data providing units or sensors 70 to obtain data about the patient such as central body temperature, activity level or body posture and environment factors that may influence the heart rate such as atmospheric pressure. The data providing units 70 includes, for example, sources of information about the patient's central body temperature, i.e. a thermometer, and activity level, e.g. an accelerometer.

Control signals from the microcontroller 51 determine when the cardiac data recording module 62 and/or data collecting module 64 collects signals, stores them in the memory or transmit them to the analyzing module 60. The cardiac data recording module 62 is coupled to the right atrial lead 14, the coronary sinus lead 16, and the right ventricular lead 18 to sample cardiac signals across any combination of electrodes.

The microcontroller 51 includes timing control circuitry 56 to control timing of the stimulation pulses (e.g. pacing rate, AV delay, VV delay, etc.) as well as to keep track of timing of refractory periods blanking intervals, etc., which is well known in the art. In addition, the microcontroller 51 may include components such as e.g. an arrhythmia detector (not shown). Furthermore, the timing control circuitry 56 controls the selection of electrode configuration, i.e. pacing sites, used for delivering the stimulation pulses.

Furthermore, the microcontroller 51 is coupled to a memory 49 by a suitable data/address bus (not shown), wherein the programmable operating parameters used by the microcontroller 51 are stored and modified, as required, in order to customize the operation of the cardiac stimulator to the needs of a particular patient. Such operating parameters define, for example, pacing pulse amplitude, pulse duration, etc. Advantageously, the operating parameters may be non-invasively programmed into the memory 49 through a communication module 66 including, for example, a telemetry circuit for telemetric communication via communication link 63 with an external device 68, such as a programmer or a diagnostic system analyzer. The telemetry circuit 66 advantageously allows intracardiac electrograms and status information relating to the operation of the device 10 to be sent to the external device 68 through an established communication link 63. Further, the communication module may alternatively or as a complement to the telemetry circuit include circuit for RF communication.

Moreover, the cardiac stimulator 10 additionally includes a battery 65 that provides operating power to all of the circuits shown in FIG. 1. Preferably, the stimulator 10 employs lithium or similar battery technology.

The analyzing module 60 is configured to determine whether a recorded sinus rate value satisfies predetermined measurement conditions. If a sinus rate value is considered to be valid, i.e. satisfies the measurement conditions, it is used to trend the sinus rate. However, if the measurement conditions are not met, i.e. are not satisfied, the sinus rate value is discarded from further analysis. Hence, only valid sinus rate values are used for trending the sinus rate over time.

Each sinus rate value is preferably created as a median value or average value of the sinus rate of a relatively high number of cardiac cycles, for example, during a period of 10-60 minutes.

Based on a trend analysis, the analyzing module 60 determines a preferred pacing therapy providing a lowest sinus rate.

The aforementioned component or components of the microcontroller 51 may be implemented as part of the microcontroller 51, or as software/firmware instructions programmed into the device and executed on the microcontroller 51 during certain modes of operation.

With reference to FIG. 2, one implementation of a system according to the present invention including an implantable cardiac stimulator as described in FIG. 1 connectable to one or more medical leads will be discussed. In FIG. 2, a number of leads including a number of electrodes are shown and the present invention can be used to optimize the electrode configuration. The optimal electrode configuration and the optimal timing intervals (pacing intervals) can be determined by applying the automatic and iterative programming of the pacing therapy settings with guidance of the sinus rate values, in particular by minimizing the sinus rate, in accordance with the present invention. As the skilled person realizes, the system implementation shown in FIG. 2 is only exemplary.

The implantable cardiac stimulator 10 is in electrical communication with a patient's heart 12 by way of three leads 14, 16, and 18 suitable for delivering multichamber stimulation therapy.

To sense atrial signals and to provide right atrial chamber stimulation therapy, the stimulator 10 is coupled to an implantable right atrial lead 14 having, for example, an atrial tip electrode 71, which typically is implanted in the patient's right atrial appendage or septum. FIG. 1 shows the right atrial lead 14 as also having an atrial ring electrode 72.

The cardiac stimulator 10 is in electrical communication with the heart 12 by way of an implantable right ventricular lead 18 having, in this embodiment, a right ventricular tip electrode 73 and right ventricular ring electrodes 74a-74c. Typically, the right ventricular lead 18 is transvenously inserted into the heart 12 to place the right ventricular tip electrode 73 in the right ventricular apex. The right ventricular lead 18 is capable of sensing or receiving cardiac signals, and delivering stimulation in the form of pacing therapy.

The cardiac stimulator 10 may further sense left atrial and ventricular cardiac signals and provide left chamber pacing therapy via the coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The coronary sinus lead 16 is designed to receive atrial and ventricular pacing signals and to deliver left ventricular pacing therapy using, for example, a left ventricular tip electrode 75 and left ventricular ring electrodes 76a-76c, and deliver left atrial pacing therapy using a left atrial ring electrode 24.

In operation, the cardiac stimulator 10 obtains data about the heart 12 via the leads 14, 16 and 18 and possibly via other data providing units. This data is provided to the internal processor 51 (see FIG. 1), which analyses the data and provides a response as appropriate. In particular, the cardiac stimulator 10 generates one or more therapy signals that are preferably optimized in accordance with the obtained data.

Figure 3:
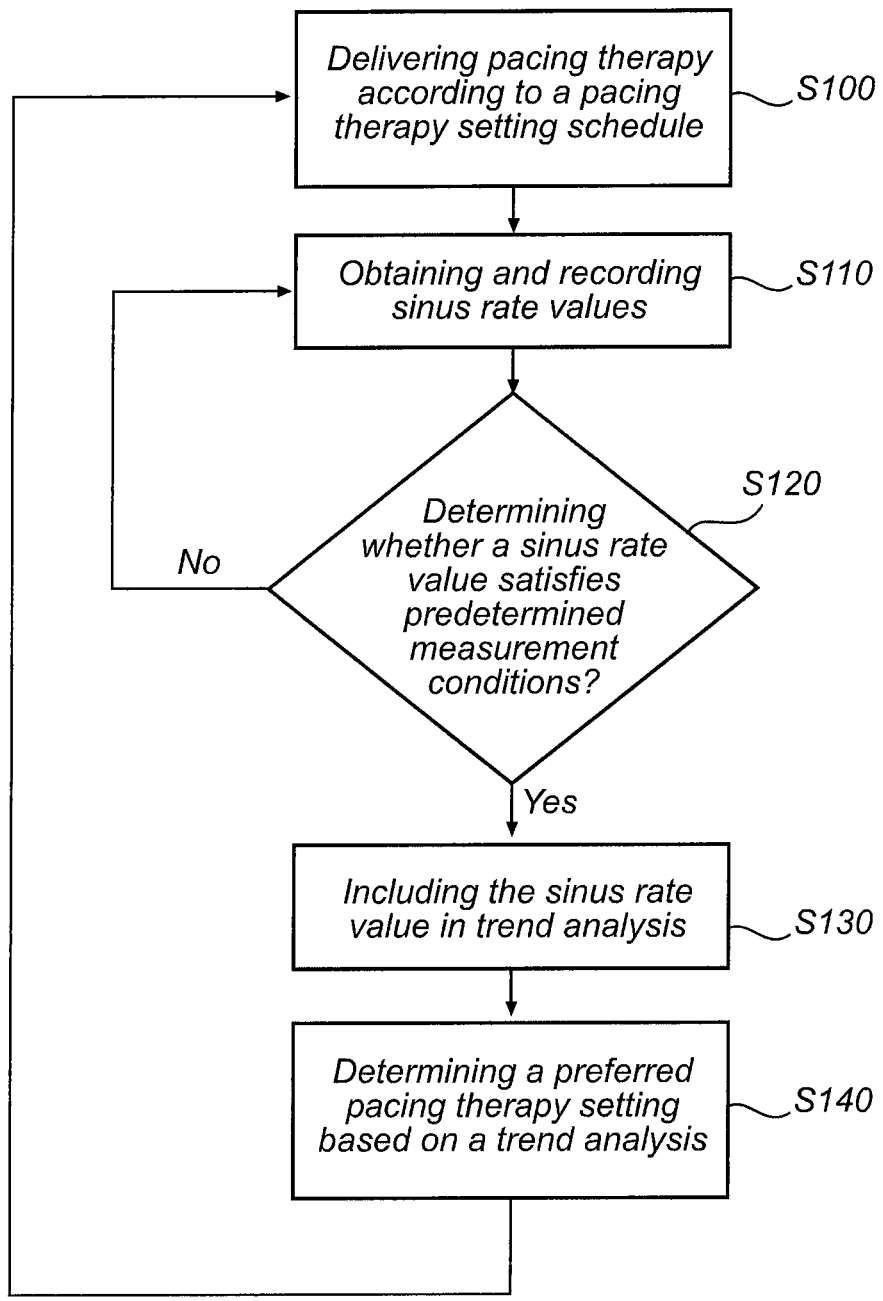
FIG. 3 is a flow diagram describing an embodiment of a method according to the present invention.
Figure 5:
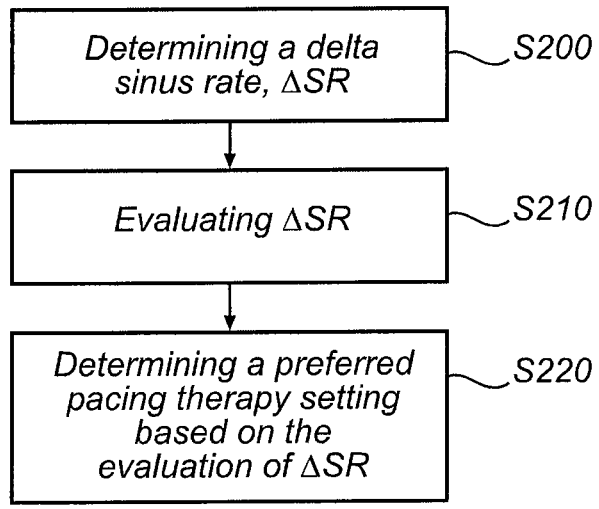
FIG. 5 is a flow diagram describing aspects of the method according to the present invention shown in FIG. 3
Figure 8:
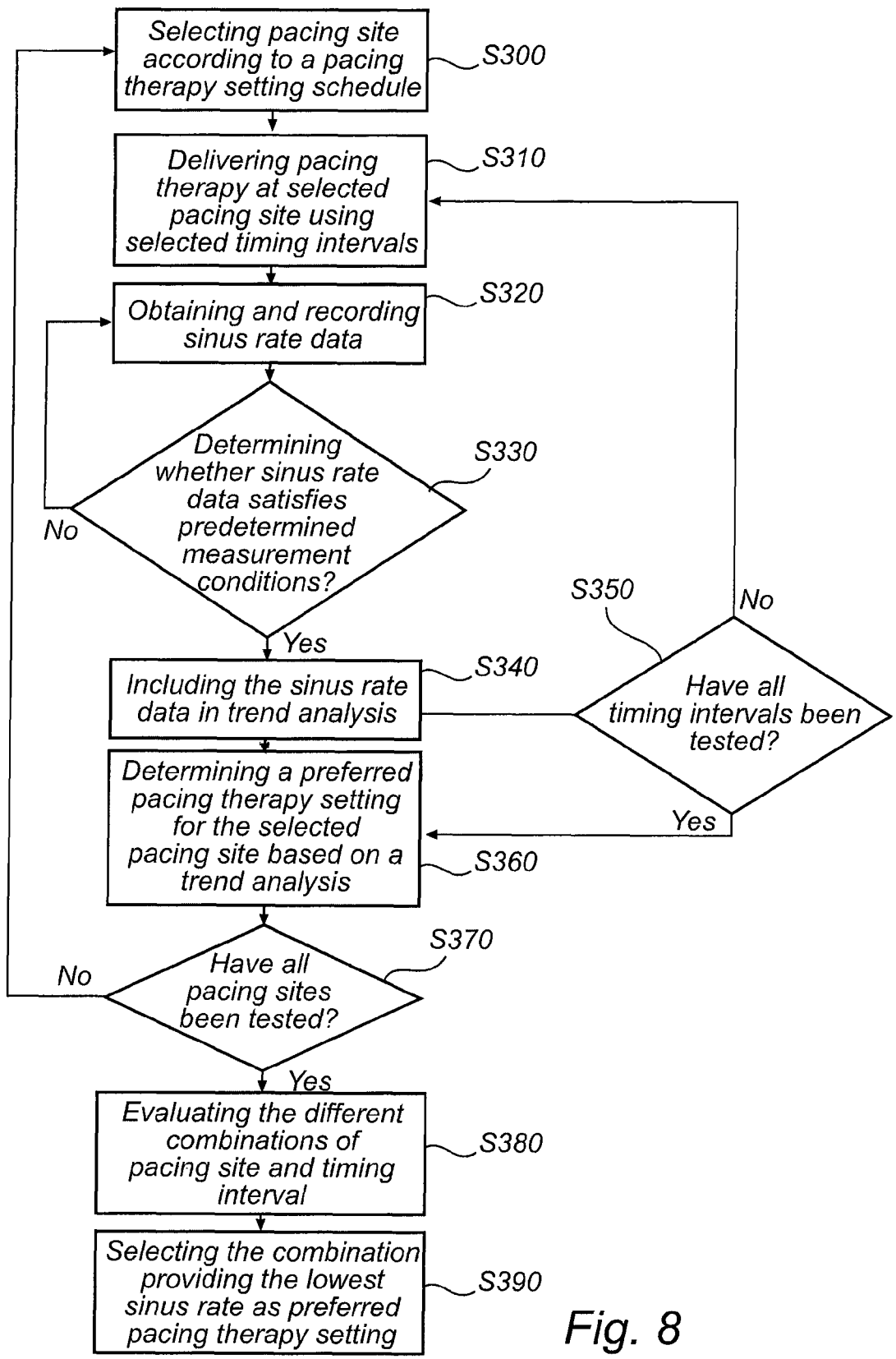
FIG. 8 is a flow diagram describing an embodiment of a method according to the present invention.

Turning now to FIG. 3, an embodiment of the method according to the present invention will be discussed. The flow charts shown in FIGS. 3, 5, and 8 are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern medical device, given the disclosure herein, is within the abilities of the person skilled within the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as RAM, ROM, CD-ROM, NVRAM, EEPROM, flash memory, and the like. The instructions may be implemented as one or more software modules, which may be executed by themselves or in combination with other software.

First, in step S100, pacing therapy is delivered to the heart according to a pacing therapy setting schedule comprising delivering therapy using specific pacing intervals and specific electrode configurations.

In step S110, sinus rate values corresponding to the sinus rate over at least one cardiac cycle is obtained and recorded.

In step S120, a check is performed for each recorded sinus rate value to evaluate or determine whether the sinus rate values satisfy predetermined measurement conditions. Only sinus rate values recorded at acceptable measurement conditions are used in the trend analysis. To determine whether the measurement conditions are acceptable or not, a number of measurement condition parameters are measured, preferably synchronously, with the measurement of the sinus rate including, for example, activity level, central body temperature, atmospheric pressure, body posture. The measurement condition parameters may indicate acceptable measurement conditions if an activity level of the patient being below a predetermined level, and/or a central body temperature of the patient being within predetermined limits, and/or an atmospheric pressure being within predetermined limits, and/or a measurement was performed (i.e. the sinus rate value was recorded) at a specific body posture; and/or a measurement was performed (i.e. the sinus rate value was recorded) during a specific period of time of a day.

Thus, the measurement conditions include, but are not limited to, that the activity level of the patient is within predetermined limits and/or that the central body temperature of the patient is within predetermined limits and/or that the atmospheric pressure is within predetermined limits and/or that the patient is positioned in a predetermined body posture. Furthermore, circadian variations can be avoided by measuring during the same time of the day, for example, when the patient is at rest during night-time.

If the sinus rate value satisfies the measurement conditions, the sinus rate value is considered valid for use in trending the sinus rate over time and is included into the analysis in step S130. In step S140, sinus rate changes over time are analyzed to identify a preferred pacing therapy setting.

However, if the sinus rate value does not satisfy the measurement conditions, the sinus rate value is discarded and is not used in the trend analysis. The algorithm returns to step S110 to obtain and record new sinus rate values.

Figure 4:
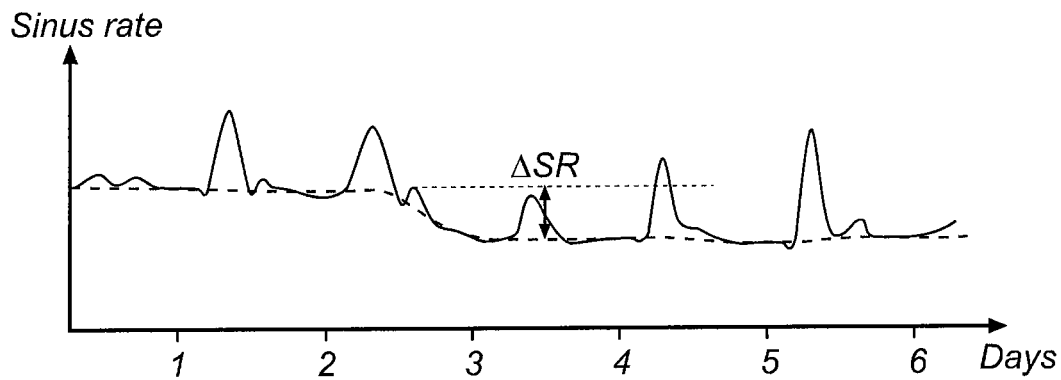
FIG. 4 is a diagram showing changes of the sinus rate over time.

In FIG. 4, a diagram illustrating the sinus rate trended over time is shown. The sinus rate over a number of days is illustrated and as can be seen, a shift in the sinus rate (average or median sinus rate) occurred after about three days. After the shift, the sinus rate has a lower level, which is an improvement in the functioning of the heart. The shift may be the result of a change of the pacing therapy settings leading to an improved pacing therapy or may have been caused by changes in physiological factors of the patient or environmental factors. For example, a decrease in the adrenaline level may cause a decrease of the sinus rate, which effect however declines relatively fast. Similarly, a sudden increase of the sinus rate may be caused by change of the pacing therapy settings, however in this case leading to an impaired pacing therapy, or by changes in physiological factors of the patient or environmental factors. For example, a local heart defect such as a coronary artery occlusion or non-synchronous contractions caused by a block in the conduction system may lead to an increased sinus rate. According to the present invention, factors that may influence the sinus rate such as activity level or central body temperature are sensed and only sinus rate values obtained during acceptable measurement conditions are accepted in the optimization process. Thereby, the risk of an influence of the sinus rate that is not a result of a pacing therapy setting change can be reduced.

Figure 6:
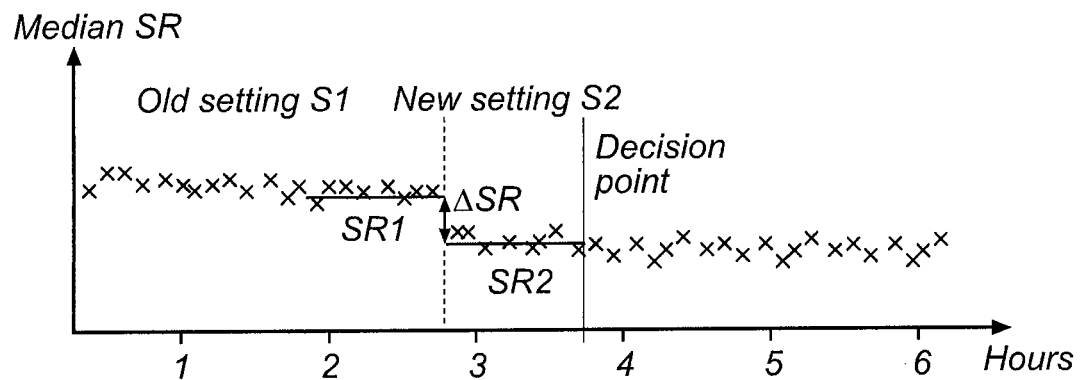
FIG. 6 is a diagram showing changes of the median sinus rate caused by an adjustment of the pacing therapy settings.
Figure 7:
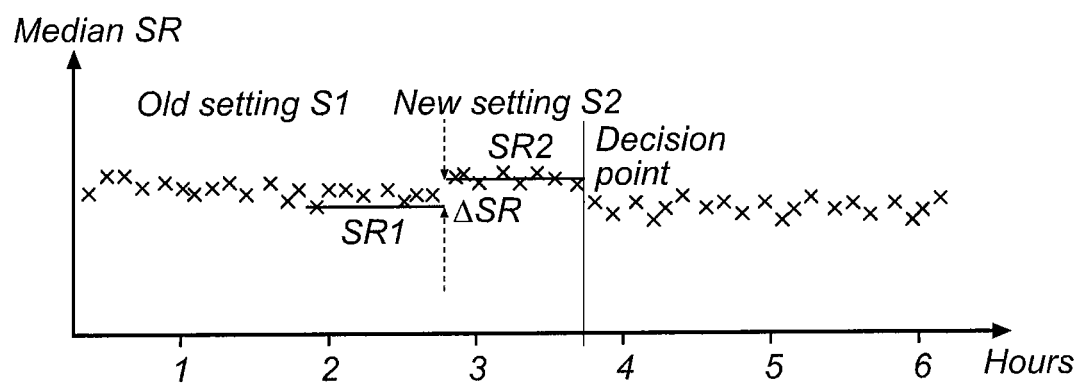
FIG. 7 is a diagram showing changes of the median sinus rate caused by another adjustment of the pacing therapy settings.

With reference now to FIGS. 5-7, an embodiment of the trend analysis performed, for example, in steps S130 and S140 of FIG. 3 will be discussed. In FIG. 5, a flow chart illustrating the steps of the method is shown and, in FIGS. 6 and 7, diagrams showing the median sinus rate over time are shown.

First, in step S200, a delta sinus rate (or difference sinus rate), $\Delta SR$, is determined as the difference between an average sinus rate for a current pacing therapy setting, SR2, and an average sinus rate for the preceding pacing therapy setting, SR1, i.e. $\Delta SR=SR2-SR1$ (of course $\Delta SR$ can alternatively be defined as $SR1-SR2$). For example, each average sinus rate, SR, used in the trend analysis may be determined over a period of time of 10-60 minutes, which, in turn, is calculated from a number of sinus rate values, which are indicated with x in FIGS. 6 and 7.

In step S210, at a predetermined decision point (which, for example, may occur every 12, 24, 48, or 72 hour), $\Delta SR$ is evaluated. SR2>SR1, i.e. the new pacing therapy setting provides a higher sinus rate than the previous pacing therapy setting, indicates that the new pacing therapy setting impairs the functioning of the heart. That is, according to the above definition of $\Delta SR$, a positive $\Delta SR$, i.e. SR2>SR1, indicates that the median sinus rate of the new pacing therapy setting is higher than the median sinus rate of the previous pacing therapy setting. This situation is illustrated in FIG. 7. The median sinus rate increases when the new pacing therapy setting, S2, is introduced compared to the median sinus rate at the previous pacing therapy setting, S1.

However, if SR1>SR2, i.e. the previous pacing therapy setting provides a higher median sinus rate compared to the median sinus rate of the new pacing setting. This situation is illustrated in FIG. 6. The median sinus rate decreases when the new pacing therapy setting, S2, is introduced compared to the previous pacing therapy setting, S1.

In the illustrated situations in FIGS. 6 and 7, $\Delta SR$ was determined based on SR1 and SR 2, which, in turn, are based on an average of the sinus rate values recorded during one hour of measurement. This is of course an arbitrary selection, and, for example, 0.5, 1.5 or 2 hours may alternatively be used to determine an average or median sinus rate.

In step S220, a preferred pacing therapy setting is determined based on the evaluation of ΔSR. According to this embodiment, the new pacing therapy setting is kept if ΔSR is negative and the pacing parameters are reprogrammed to the parameters of the previous pacing therapy setting if ΔSR is positive. This is illustrated in FIGS. 6 and 7, respectively. In FIG. 7, where a situation where the new pacing therapy setting, S2, provides a higher median sinus rate than the previous pacing therapy setting, S1, is illustrated, the device is reprogrammed to the previous pacing therapy setting so as to reduce the sinus rate again. In FIG. 6, where a situation where the new pacing therapy setting, S2, provides a lower median sinus rate than the previous pacing therapy setting, S1, the new pacing therapy setting is kept so as to maintain the lower sinus rate.

The selected pacing therapy setting is kept until a new pacing therapy setting is programmed in accordance with the pacing therapy setting schedule. For example, a new pacing therapy setting may be programmed after a period of time of 48 or 60, or 72 hours.

With reference now to FIG. 8, another embodiment of the method for optimizing pacing therapy settings according to the present invention will be discussed. FIG. 8 illustrates a flow chart describing the steps of the embodiment of the method. The method according to this embodiment includes an optimization of both pacing site and timing intervals.

First, in step S300, a first electrode configuration is selected for delivery of pacing stimulation, for example, a specific electrode configuration on a multi-polar lead such as a quadpole lead or endocardial, sub-endocardial, epicardial or intramural poles according to the pacing therapy setting schedule. In step S310, pacing stimulation is delivered via the selected electrode configuration using a first pacing therapy setting, for example, a first AV interval or a first VV interval.

In step S320, sinus rate data is obtained and recorded, for example, a sinus rate value is recorded for each cardiac cycle or for a number of cardiac cycles.

In step S330, a check is performed for each recorded sinus rate value to evaluate or determine whether the sinus rate value satisfies predetermined measurement conditions. Only sinus rate values recorded at acceptable measurement conditions are used in the trend analysis. To determine whether the measurement conditions are acceptable or not, a number of measurement condition parameters are measured synchronously with the measurement of the sinus rate including, for example, activity level, central body temperature, atmospheric pressure, body posture. The measurement condition parameters may indicate acceptable measurement conditions if an activity level of the patient is below a predetermined level, and/or a central body temperature of the patient is within predetermined limits, and/or an atmospheric pressure is within predetermined limits, and/or a measurement was performed (i.e. the sinus rate value was recorded) at specific body posture; and/or a measurement was performed (i.e. the sinus rate value was recorded) during a specific period of time of a day.

Hence, the measurement conditions include, but are not limited to, that the activity level of the patient is within predetermined limits and/or that the central body temperature of the patient is within predetermined limits and/or that the atmospheric pressure is within predetermined limits and/or that the patient is positioned in a predetermined body posture.

Furthermore, circadian variations can be avoided by measuring during the same time of the day, for example, when the patient is at rest during night-time.

If the sinus rate value satisfies the measurement conditions, the sinus rate value is considered to be valid for use in trending the sinus rate over time in step S340 and for analysis of sinus rate changes in step S360. However, if a sinus rate value does not satisfy the measurement conditions that sinus rate value is discarded and is not used in the trend analysis.

In step S350, it is checked whether all timing intervals according to the pacing therapy setting schedule have been applied, i.e. have been tested, or, alternatively, whether sinus rate data has been obtained for all timing intervals.

If yes, the algorithm proceeds to step S360 where it is determined which timing interval setting, for the specific pacing, that provides the lowest sinus rate. This timing interval is selected together with the present pacing site (electrode configuration) as preferred pacing therapy setting.

If no, the algorithm returns to step S310 for reprogramming to the next timing interval setting according to the pacing therapy setting schedule. In case no valid sinus rate values has been obtained for a specific timing interval, that timing interval setting may be programmed again in order to enable a recording of valid sinus rate data for that specific timing interval setting.

Thereafter, at step S370, it is checked whether all pacing sites according to the pacing therapy setting schedule have been tested or, alternatively, whether an optimal timing interval has been found for each pacing site. If no, the algorithm returns to step S300 where the next electrode configuration in the pacing therapy setting schedule is selected for use in delivery of pacing stimulation. If it is found that no valid sinus rate values were found for a specific timing interval at the selected electrode configuration, that timing interval setting may in an alternative embodiment be programmed again to enable a recording of valid sinus rate values. Hence, in that case, the algorithm may return to step S310 instead.

In step S380, the different combinations of pacing site (electrode configuration) and timing interval are evaluated to find the combination providing the lowest sinus rate.

Thereafter, in step S390, the combination providing the lowest sinus rate is selected as preferred pacing therapy setting.

Preferably, the algorithm is adapted to continuously make parameter changes, for example, according to the method described with reference to FIG. 8. To this end, the procedure may return to step S300 and initiate a new evaluation loop, for example, after a predetermined period of time, e.g. after 24, 48 or 72 hours.

The present invention can be implemented to test suggested reprogramming of the device parameters when the patient is at rest for a period of time in connection with optimization at a follow up situation. The physician may be presented with the results how each reprogramming affected the rest rate.

The present invention also provides an automatic optimization, for example, within limits defined by the physician. Thereby, the therapy can continuously be adjusted to changing electrical and mechanical properties of the heart caused by, for example, cardiac remodelling or reverse remodelling.

Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claimed is:

1. A system for pacing therapy optimization of a cardiac stimulator implanted in a patient, said system comprising:
   a cardiac pacing delivery module configured to deliver cardiac pacing therapy stimulation to at least one chamber of the heart using specific pacing intervals via a specific electrode configuration, over a range of cardiac pacing therapy settings;
   a cardiac data recording module configured to record sinus rate values over at least one cardiac cycle for different cardiac pacing therapy settings;
   an analyzing module configured to:
   determine whether a sinus rate value satisfies predetermined measurement conditions;
   trend the sinus rate over time using sinus rate values satisfying the predetermined measurement conditions; and
   determine a preferred cardiac pacing therapy providing a lowest sinus rate based on a trend analysis of the sinus rate.

2. The system according to claim 1, wherein
   said cardiac pacing delivery module is configured to deliver cardiac pacing therapy via at least two different electrode configurations and over a range of pacing intervals for each electrode configuration;
   said cardiac data recording module is configured to record sinus rate values over at least one cardiac cycle for each pacing interval for each electrode configuration; and wherein
   said analyzing module is configured to:
      determine whether a sinus rate value satisfies predetermined measurement conditions;
      trend the sinus rate over time using sinus rate values satisfying the predetermined measurement conditions; and
      determine a preferred cardiac pacing therapy setting including a preferred electrode configuration and a preferred pacing interval providing a lowest sinus rate based on a trend analysis of the sinus rate.

3. The system according to claim 1, wherein
   said analyzing module is configured to:
   analyze the trended sinus rate values to determine changes in the sinus rate, wherein a change is determined if an increased or decreased sinus rate persists at least a predetermined period of time and/or exceeds a first predetermined threshold or is below a second predetermined threshold, respectively; and
   instruct said cardiac pacing delivery module to select the cardiac pacing therapy setting that has been determined to provide the lowest sinus rate for delivery of cardiac pacing therapy until next pacing therapy setting adjustment occurs according to said pacing therapy setting schedule.

4. The system according to claim 1, further comprising a data collecting module configured to gather measurement condition information of at least one measurement condition parameter; and
   wherein said analyzing module is configured to:
      determine that a sinus rate value satisfies said predetermined measurement conditions if a value of said at least one measurement condition parameter indicates acceptable measurement conditions.

5. The system according to claim 4, wherein said analyzing module is configured to:
   determine that a sinus rate value do not satisfy said predetermined measurement conditions if said at least one measurement condition parameters indicates that the measurement conditions are not acceptable.

6. The system according to claim 1, wherein said analyzing module is configured to determine at least one median or average sinus rate value over a predetermined number of cardiac cycles for each cardiac pacing therapy setting.

7. The system according to claim 1, wherein said measurement condition parameters comprises:
   an activity level of said patient; and/or
   a central body temperature of said patient; and/or
   an atmospheric pressure; and/or
   a body posture of said patient; and/or
   time point for measurement.

8. The system according to claim 7, wherein said measurement conditions parameters indicates acceptable measurement conditions if:
   an activity level of said patient being below a predetermined level; and/or
   a central body temperature of said patient being within predetermined limits; and/or
   an atmospheric pressure being within predetermined limits; and/or
   a measurement was performed at specific body posture; and/or
   a measurement was performed during a specific period of time of a day.

9. The system according to claim 1, wherein said analyzing module is further configured to:
   compare a value of the sinus rate determined over a predetermined period of time recorded at a previous cardiac pacing therapy setting with a value of the sinus rate determined over a predetermined period of time recorded at a present cardiac pacing therapy setting; and
   select the cardiac pacing therapy setting providing the lowest value of the sinus rate as the preferred cardiac pacing therapy setting.

* * * * *